(12) United States Patent
von Grote et al.

(10) Patent No.: US 11,318,320 B2
(45) Date of Patent: May 3, 2022

(54) CONNECTOR CAVITY ASSEMBLY FOR A MEDICAL DEVICE AND MANUFACTURING METHOD

(71) Applicant: BIOTRONIK SE & Co. KG, Berlin (DE)

(72) Inventors: Markus von Grote, Berlin (DE); Marina Ruschel, Berlin (DE); Rolf Klenner, Michendorf (DE)

(73) Assignee: BIOTRONIK SE & Co. KG, Berlin (DE)

( * ) Notice: Subject to any disclaimer, the term of this patent is extended or adjusted under 35 U.S.C. 154(b) by 59 days.

(21) Appl. No.: 16/871,415

(22) Filed: May 11, 2020

(65) Prior Publication Data
US 2020/0360700 A1 Nov. 19, 2020

(30) Foreign Application Priority Data
May 15, 2019 (EP) ..................... 19174589

(51) Int. Cl.
*A61N 1/375* (2006.01)
*A61N 1/36* (2006.01)
*A61N 1/05* (2006.01)
*A61N 1/372* (2006.01)
*A61N 1/378* (2006.01)
(Continued)

(52) U.S. Cl.
CPC .......... *A61N 1/3752* (2013.01); *A61N 1/0563* (2013.01); *A61N 1/36125* (2013.01); *A61N 1/378* (2013.01); *A61N 1/37229* (2013.01); *A61N 1/37512* (2017.08); *B29C 45/14418* (2013.01); *B29C 45/14639* (2013.01);
(Continued)

(58) Field of Classification Search
CPC .............. A61N 1/3752; A61N 1/37512; A61N 1/0563; A61N 1/36125; A61N 1/37229; A61N 1/378; H01R 24/58; H01R 13/5224; H01R 13/187; H01R 2201/12; B29C 45/14418; B29C 45/14639; B29C 2045/169; Y10T 29/49208
See application file for complete search history.

(56) References Cited

U.S. PATENT DOCUMENTS 8,091,226 B2    1/2012  Sjostedt et al.
11,058,882 B2 * 7/2021  Deininger .......... A61N 1/36062
(Continued)

OTHER PUBLICATIONS

European Search Report and Annex to the European Search Report on European Patent Application No. EP 19 17 4589.2, dated Nov. 18, 2019 (10 pages).

*Primary Examiner* — Catherine M Voorhees
(74) *Attorney, Agent, or Firm* — Buchanan Ingersoll & Rooney PC

(57) ABSTRACT

A connector cavity assembly for a medical device, comprising at least one connector cavity comprising a plurality of electrically conductive electrode contacts spaced apart from each other and a plurality of electrically insulating insulation elements, wherein the electrode contacts and the insulation elements are arranged alternatingly; and a connector cavity housing. The connector cavity assembly is characterized in that the at least one connector cavity is removably arranged within the connector cavity housing, wherein the connector cavity housing exerts a pretension on the at least one connector cavity leading to a liquid-tight sealing between the insulation elements and the electrode contacts.

15 Claims, 5 Drawing Sheets

(51) Int. Cl.
*B29C 45/14* (2006.01)
*H01R 24/58* (2011.01)
*B29C 45/16* (2006.01)
*H01R 13/52* (2006.01)

(52) U.S. Cl.
CPC ........ *H01R 24/58* (2013.01); *B29C 2045/169* (2013.01); *H01R 13/5224* (2013.01)

(56) References Cited

U.S. PATENT DOCUMENTS

| | | | |
|---|---|---|---|
| 11,139,603 B2* | 10/2021 | Conger | H01R 13/111 |
| 2008/0255631 A1* | 10/2008 | Sjostedt | H01R 13/187 |
| | | | 607/37 |
| 2009/0258519 A1* | 10/2009 | Dilmaghanian | H01R 13/40 |
| | | | 439/271 |
| 2019/0299014 A1* | 10/2019 | Lim | A61N 1/3754 |

* cited by examiner

CONNECTOR CAVITY ASSEMBLY FOR A MEDICAL DEVICE AND MANUFACTURING METHOD

CROSS-REFERENCE TO RELATED APPLICATIONS

This patent application claims the benefit of and priority to co-pending European Patent Application No. EP 19174589.2, filed on May 15, 2019 in the European Patent Office, which is hereby incorporated by reference in its entirety.

TECHNICAL FIELD

The present invention relates to a connector cavity assembly for a medical device, to a medical device comprising such a connector cavity assembly, to a method for manufacturing such a connector cavity assembly, and to a method for manufacturing a medical device comprising such a connector cavity assembly.

BACKGROUND

Connector cavities are used for receiving a connector or a plug to establish an electric connection between two parts, such as a medical device and an electrode.

Connector cavities used in medical devices typically comprise metallic rings or other electrically conductive elements that serve as contact elements. These rings are spaced apart from each other, wherein electrically insulating components are placed between them. In an axial direction of such a connector cavity, an alternating series of a ring, an insulator, another ring, another insulator, etc. is established. Such a connector cavity is intended to be embedded into a resin, such as an epoxy resin.

To keep the individual conductive and insulating components of the connector cavity in place, the individual components are typically threaded onto a mandrel. This mandrel is then removed during or immediately after embedding the connector cavity into a resin.

For embedding the connector cavity into a resin, it is necessary that the insulating components are in close contact with the electrically conductive components, e.g., the rings. Therefore, an axial tensioning needs to be applied to such a connector cavity. Then, it is impossible for a resin to enter an interior space within the connector cavity.

For applying an appropriate pretensioning of such connector cavities, pretensioning devices are typically used. These pretensioning devices exert a pretensioning force until the resin is casted over the connector cavity and can exert the necessary pretensioning force itself. However, such handling makes the manufacturing process of medical devices with embedded connector cavities difficult. On the one hand, an additional external pretensioning device is necessary until the resin is cast around the connector cavity. Furthermore, the timing of removing the external pretensioning device is sophisticated as it depends on the hardening or curing properties of the used resin.

It is also known to perform a pre-casting step prior to the actual casting step in order to have the connector cavity placed in the right position with a sufficient pretension. However, this requires a two-step manufacturing method increasing the overall manufacturing costs.

If a (medical) device is to be equipped with more than one connector cavity, the relative arrangement of the individual connector cavities can only be carried out in the mold used for embedding the connector cavities into a resin. Due to unavoidable deviations of this arrangement, manufacturing tolerances of such components are relatively high.

At this stage of the manufacturing process, other components like an antenna, wiring ribbons or distance elements are typically placed around and connected to the connector cavities under very narrow spatial conditions leading to an overall difficult manufacturing process.

The present invention is directed at overcoming one or more of the above-mentioned problems.

SUMMARY

Thus, it is an object of the present invention to provide a device and a method facilitating the manufacturing process of a medical device comprising a connector cavity.

At least this object is generally achieved by a tensioning tool for connector cavities of a medical device designed to be incorporated into, e.g. a header of an implantable medical device, particularly a connector cavity housing being designed to receive at least one connector cavity comprising a plurality of electrically conductive electrode contact and a plurality of insulating elements, which are alternatingly arranged, wherein the connector cavity housing is furthermore designed to exert a pretension on the least one connector cavity, particularly such that a liquid-tight sealing, and particularly a potential separation, between the insulating elements and the electrode contact is realized or present, and wherein the connector cavity is removably arrangeable in the connector cavity housing. Preferably, the tensioning tool or connector cavity housing comprises receiving means or portion for receiving the electrically conductive electrode contacts and/or the insulating element, for example bars, arranged on the inside of the housing, which guide the aforementioned contacts or insulating elements into a desired position.

Particularly, at least the above object is achieved with a connector cavity assembly having the claim elements of claim 1. Such a connector cavity assembly is particularly appropriate for a medical device. It comprises at least one connector cavity and a connector cavity housing for receiving this connector cavity. The connector cavity comprises a plurality of electrically conductive electrode contacts spaced apart from each other. Furthermore, it comprises a plurality of electrically insulating insulation elements. Thereby, the electrode contacts and the insulation elements are arranged alternatingly. Both the electrode contacts and the insulation elements can be ring-shaped so that placing electrode contacts and insulation elements alternatingly above each other leads to a cylindrical shape of the connector cavity. Then, a central axis is defined extending in the longitudinal direction of the connector cavity.

According to an aspect of the present invention, the at least one connector cavity is removably arranged within the connector cavity housing. In order to achieve a save positioning of the connector cavity within the connector cavity housing and in order to achieve a sealing abutment of the insulation elements at the electrode contacts, the connector cavity housing is dimensioned such that it exerts a pretension on the at least one connector cavity. This pretension leads to a compression of the insulation elements. It is typically directed along a longitudinal axis of the connector cavity, i.e., it is an axial pretension. The compression serves for a liquid-tight sealing between the insulation elements and the electrode contacts. Particularly, insulating elements serves as seal to protect the connector cavity against intruding resin during molding process to yield the final header as well as to ensure a proper potential separation between two electrode contacts.

Expressed in other words, the connector cavity housing and the connector cavity have dimensions that are adjusted with respect to each other. Then, it is guaranteed that the connector cavity housing exerts a sufficiently high pretension onto the inserted connector cavity to establish a sealing between the insulation elements and the electrode contacts. Particularly, the connector cavity housing has an internal space configured to receive the connector cavity, wherein the internal space has a longitudinal length that is smaller than the longitudinal length of the connector cavity in its uncompressed state.

The connector cavity housing can be made of any rigid, electrically non-conductive or insulating material, particularly a rigid plastic such as a polyarylethersulfone (PAES), for example, like polysulfone (PSU, CAS No. 25135-51-7) or polyethersulfone (PES, CAS No. 25608-63-3), a polyaryletherketone, for example, polyether ether ketone (CAS No. 29658-26-2) or a acrylonitrile butadiene styrene (CAS No. 9003-56-9). Preferably, the connector cavity housing is made of injection moldable plastic.

The insulation elements can be made from any compressible (or elastic) electrically insulating material. For example, silicone is very appropriate material. The electrode contacts can be made from any electrically conductive material. Typically, metallic materials are appropriate materials for the electrode contacts. To give an example, the electrode contracts can comprise a metal spring, e.g., a ring-shaped metal spring, surrounded by a compact metal material, e.g., also having a ring shape.

In an embodiment, the dimensions of a connector cavity receiving portion of the connector cavity housing is adjustable. To give an example, a spring element or an actuator can be provided in order to automatically adjust the dimensions of the receiving portion of the connector cavity housing to the inserted connector cavity. The spring force of an according spring needs to be equal to or higher than a pretensioning force necessary for achieving a compression of the insulation elements leading to a sealing abutment of the insulation elements at the electrode contacts.

In an embodiment, the at least one connector cavity extends in a longitudinal direction from a proximal end to a distal end. Thereby, it comprises a proximal end element positioned at the proximal end and a distal end element positioned at the distal end. The proximal end element and the distal end element act as stops for the connector cavity. They can be made from plastic material, in particular from a non-elastic plastic material. Thermoplastic, particularly rigid, material such as polyarylethersulfones (PAES) like polysulfone (PSU) polyethersulfone (PES), polyaryletherketones, for example, polyether ether ketone (CAS No. 29658-26-2) or an acrylonitrile butadiene styrene (CAS No. 9003-56-9) are particularly appropriate materials.

The proximal end element and/or the distal end amend can be loosely connected with the remaining parts of the connector cavity (i.e., they can be detachably arranged at the remaining parts of the connector cavity) or they can be fixedly attached to the remaining parts of the connector cavity, e.g., by gluing them to the remaining parts of the connector cavity. Thereby, the proximal end element and/or the distal end element can be in direct contact with an electrode contact or in direct contact with an insulation element. Is also possible that one of the proximal end element and the distal end element is in contact with an electrode contact, whereas the respective other element is in contact with an insulation element.

In an embodiment, the distal end element is configured to receive the distal end of an electrode connector or plug and serves particularly as a mechanical stop for the distal end of the electrode connector or plug. Preferably, the distal end element is made of a rigid, preferably non-conductive material as described above.

In an embodiment, the proximal end element is designed as a terminal socket, particularly configured to receive the tip of an electrode or more specifically the tip of an electrode connector or plug. Preferably, the proximal end element comprises a fixing means configured to mechanically fix the electrode connector or plug tip, such as for example a screw thread and optionally a corresponding screw. Accordingly, in an embodiment, the proximal end element is designed as a screw block configured to receive a tip of an electrode or electrode connector or plug. Preferably, the proximal end element is made of an electrically conductive material, preferably a biocompatible metal or metal alloy. Advantageously, the proximal end element designed as terminal socket may provide an additional electrical contact to the electrode.

In an embodiment, the connector cavity housing is at least in contact with the proximal end element and the distal end element of the connector cavity. Thus, it can also contact any other elements of the connector cavity like, e.g., the insulation elements.

Preferably, any force that is exerted by the connector cavity housing on the connector cavity to achieve sufficiently high pretensioning of the connector cavity is then brought into the connector cavity mainly or solely via these end elements.

In another embodiment, the connector cavity housing is in contact with the connector cavity only via the proximal end element and the distal end element. However, the connector cavity can be in contact with other components of the medical device, particularly components of the header such as, for example, an antenna, a radiopaque tag, a wiring or the like.

In an embodiment, the connector cavity assembly comprises at least 2, 3, 4, 5, 6, 7, 8, 9, or 10 connector cavities, in particular exactly 1, 2, 3, 4, 5, 6, 7, 8, 9, or 10 connector cavities. An embodiment with at least one connector cavity, in particular exactly one, two or three connector cavities is particularly appropriate.

In an embodiment, each of the connector cavities comprises at least two to eight electrode contacts, particularly exactly two, four or eight electrode contacts, wherein each of the electrodes is separated from each other by one insulating element.

In an embodiment, the connector cavity assembly comprises at least two connector cavities, in particular exactly two connector cavities, which are offset to each other in a longitudinal direction and/or in a transversal direction of the connector cavity housing. Such an offset of the connector cavities with respect to each other facilitates guiding electrical contact elements (such as wiring ribbons) to the individual electrode contacts of the individual connector cavities. The relative position of the two connector cavities is defined by the connector cavity housing and is not subject to variances that regularly occur in case of embedding two connector cavities into a resin without fixing them within a connector cavity housing as described in the present application.

In an embodiment, the connector cavity housing comprises at least one additional receiving portion for receiving a further component of a medical device. By such an arrangement, the connector cavity housing does not only house or receive the at least one cavity connector, but also additional components that need to be present in the medical device in question. Thus, the connector cavity housing serves in such a case as frame or support for additional components that can be assembled together outside the medical device and that can then—after assembly—be placed into a mold and embedded into a hardenable resin. In such a case, it is necessary to place only one component (namely the connector cavity housing with attached further components like the at least one connector cavity and the further components of the medical device) into the mold. It is no longer necessary to individually place the further components into the mold having a very limited working space. Therefore, providing a connector cavity housing with at least one additional receiving portion significantly reduces the manufacturing effort.

In an embodiment, the additional receiving portion enables an attachment of a further component of a medical device by a latching connection (also referred to as click connection or snap-in connection). Thus, by simply clicking-in a further component, it can be easily attached to the connector cavity housing and can be easily held by the additional receiving portion. This further facilitates manufacturing of the connector cavity assembly and of the final medical device.

In an embodiment, the connector cavity assembly comprises an antenna, a coil, particularly an inductive charging coil, and/or guideways for an external or outer wiring, for example external wiring ribbons. The antenna, the coil, and the guideways for the external wiring, particularly the external wiring ribbons, represent further components of the medical device. In an embodiment, they are received by the connector cavity housing by means of the additional receiving portion referred to above. The antenna, the coil, and the guideways for the external wiring, particularly for the external wiring ribbons, are particularly appropriate further components of the medical device if the medical device is a neurostimulator.

In an embodiment, the connector cavity housing comprises at least one spacer on its lower side. This lower side is intended to face a body portion of a medical device (e.g., the housing of the medical device) when the connector cavity housing is part of the medical device. This spacer serves for defining a distance between the connector cavity assembly and the body portion of the medical device. This reduces the required accuracy of the mold into which the connector cavity assembly is placed to be embedded into a resin. Furthermore, the spacer facilitate the mounting of the connector cavity assembly to the body portion of the medical implant (e.g., electrically connecting the external wiring ribbons to electrical connection elements such as pins extending through the feedthrough of the housing by soldering or welding). The spacer serves for placing the connector cavities at always the same distance to the body portion of the medical device. Then, the error susceptibility of the manufacturing process is reduced. This reduces the rework effort otherwise needed to obtain fully usable medical devices and thus the overall manufacturing effort.

In an aspect, the present invention relates to a medical device that comprises a connector cavity assembly according to the preceding explanations. In an embodiment, the connector cavity assembly forms part of a header of this medical device.

In an embodiment, the connector cavity assembly is embedded into hardenable resin. Thereby, a connecting port is formed in the resin so that an interior of the at least one connector cavity of the connector cavity assembly is accessible from outside the medical device. Then, a connector of a lead can be inserted or plugged through the connecting port into the interior of the connector cavity so as to establish an electric connection between the connector cavity, particularly one of the electrode contacts, and one or more electrodes comprised within the lead. The connector cavity is, in turn, electrically connected with other components of the medical device (such as a battery, a capacitor, a pulse generator and a control unit comprised within the housing of the medical device) so that the medical device together with an attached electrode or lead can be used for applying electric impulses to a person in need thereof or to transmit measured impulses from the measured tissue to a respective diagnostic module comprised within the housing of the medical device.

In an embodiment, the medical device is an implantable cardiac pacemaker, an implantable cardioverter defibrillator, or an implantable neurostimulator. Any such medical device requires at least one electrode typically comprised within a lead to be placed within or adjacent to an organ, vessel or a nerve, wherein the electrode is connected to the core of the medical device via the connector cavity of the connector cavity assembly. The above named lead may comprise up to eight electrodes, for example, in case of a neurostimulator, wherein the connector cavity then comprises a respective number of electrode contacts.

In an aspect, the present invention relates to a method for manufacturing a connector cavity assembly according to the preceding explanations. This method comprises the steps explained in the following.

In a method step, a connector cavity housing is provided.

In another method step, the connector cavity is assembled by alternatingly placing electrically conductive electrode contacts and electrically insulating insulation elements into a tensioning device or tool. As an alternative to this assembly step, a preassembled connector cavity can be placed into a tensioning device. Thereby, the preassembled connector cavity comprises alternatingly positioned electrically conductive electrode contacts and electrically insulating insulation elements.

Afterwards, a pretension is exerted on the connector cavity with the tensioning device or tool. Thus, the tensioning device or tool is particularly configured to exert a pretension along a longitudinal axis of the connector cavity.

Then, the pretensioned connector cavity is transferred into the connector cavity housing.

Then, the tensioning device or tool is released and removed. Nonetheless, a pretension of the connector cavity is still necessary. This pretension is exerted by the connector cavity housing. Thus, one allows the connector cavity housing to exert a pretension on the connector cavity. This allowing step typically occurs automatically when the connector cavity is placed inside a corresponding receiving portion of the connector cavity housing since this receiving portion is dimensioned such that the connector cavity can be placed inside the connector cavity receiving portion only after a (slight) compression that is sufficient for exerting the required pretensioning onto the connector cavity. Thus, after removing the pretensioning device or tool, the connector cavity housing serves itself as tensioning device or tool. It keeps the connector cavity under required pretension until the connector cavity housing is—together with the connector cavity—embedded into a resin and thus serves for avoiding an entry of resin into the interior of the connector cavity. The pretension is furthermore exerted by the connector cavity housing during the entire lifespan of the medical device, the connector cavity assembly forms part of.

Particularly, the tensioning device or tool may be designed in form of a clamp.

In an aspect, the step of assembling the connector cavity or the step of placing a preassembled connector into the tensioning device or tool is performed without any mandrel or comparable production tool being present in an interior space of the connector cavity. Such a mandrel is usually needed when assembling a connector cavity according to prior art techniques. Since the connector cavity housing comprises a connector cavity receiving portion that prevents an undesired movement of the individual components of the connector cavity (i.e., in particular of the electrode contacts and the insulation elements) no such mandrel is any longer necessary. Refraining from using such a mandrel or a comparable production tool reduces the manufacturing costs, since these elements are comparatively costly and need to be obtained from an external provider. The step of assembling the connector cavity into a pretensioning device can be performed by an automatic assembly machine.

The pretension provided by the connector cavity housing is a path-controlled pretension. Since the dimensions of the connector cavity housing can be very precisely controlled during the manufacturing process, the resulting pretension also shows very small variances. This distinguishes the present method from prior art methods using both path-controlled and force-controlled tensioning tools requiring always monitoring and exact adjustments of the applied pretension.

In an embodiment, the connector cavity housing is a plastic component (i.e., made of a plastic material). In a further embodiment, it is a plastic component made by injection molding. Injection molding is a particularly appropriate manufacturing method for producing a high number of articles with very low manufacturing errors. Thus, the accuracy of the manufactured articles is particularly high. This results in a defined pretension of the at least one connector cavity so that a separate monitoring of the applied pretension is no longer necessary. This facilitates the manufacturing method and simplifies the tools used for mounting the connector cavity.

The manufacturing method can be fully automated and enhances the reliability and safety of the individual processing steps. The pretensioned connector cavity (or cavities) can be handled much easier than according to prior art methods since the connector cavity housing automatically offers gripping areas that are much more resistant to damage than the individual components of the connector cavity pretensioned without connector cavity housing. Even an optically observable damage of the connector cavity housing does not yet reduce the functionality of the connector cavity housing or the connector cavity pretensioned by the connector cavity housing.

Since the connector cavity is always pretensioned to a defined extent, a cumbersome manual pretensioning of the connector cavity is no longer necessary. This significantly reduces the time necessary for the manufacturing process.

In an aspect, the present invention relates to a method for manufacturing a medical device according to the above explanations. This manufacturing method comprises the steps explained in the following.

First, a connector cavity assembly according to the preceding explanations is provided. Then, this connector cavity assembly is placed on a body of a medical device. Thereby, a detachable or non-detachable connection between the connector cavity assembly and the body of the medical device can be established.

Furthermore, an electrical contact is established between at least one electrically conductive electrode contact of the connector cavity assembly and an electronics housed in the body of the medical device, e.g. electrically connecting the external wiring ribbons to pins extending through the feedthrough of the housing of the medical device by soldering or welding. This electronics can comprise, e.g., a battery, a capacitor and a control unit and may serve for generating electric pulses to be applied to the site of action by an electrode or lead connected to the connector cavity of the connector cavity assembly.

Afterwards, a hardenable resin is casted around the connector cavity assembly so as to embed the connector cavity assembly in the resin and to tightly attach it to the body of the medical device and to provide a protective cover for the connector cavity assembly that is resistant to the condition of the intended place of action, i.e., inside of the human body. Typically, the resin fully embeds the connector cavity assembly, leaving only open a connecting port through which an interior of the connector cavity is accessible from outside the medical device.

Finally, one lets the resin harden and yields a medical device comprising a body portion and a header portion, wherein the connector cavity assembly embedded in the resin forms part of the header portion.

All aspects, variants and embodiments of the described connector cavity assembly can be transferred in an analogous way to the described medical device and to the described manufacturing methods, and vice versa. Furthermore, aspects, variants and embodiments of one manufacturing method can be transferred to the other manufacturing method, and vice versa. Thereby, all aspects, variants and embodiments can be combined in any desired way.

Further features, aspects, objects, advantages, and possible applications of the present invention will be explained in more detail and will become apparent with respect to exemplary embodiments and examples described below, in combination with the accompanying Figures and the appended claims.

DETAILED DESCRIPTION

Figure 1:
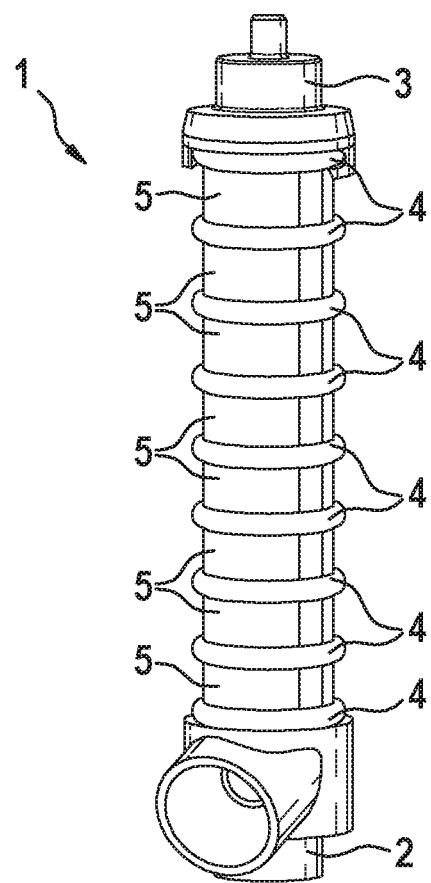
FIG. 1 shows an embodiment of a connector cavity.

FIG. 1 shows an embodiment of a connector cavity 1 comprising a distal end element 2 at its distal end and a proximal end element 3 at its proximal end. Between the distal end element 2 the proximal end element 3, a plurality of ring-shaped insulation elements 4 made from silicone and alternating metal rings 5 each comprising a metal spring in their interior are positioned. The insulating elements 4 act as spacer between the metal rings 5 and for electrically insulating two adjacent metal rings 5. The metal rings 5 act as electrode contacts.

The insulating elements 4 are compressible. The distal end element 2 and the proximal end element 3 are non-elastic. If a pressure is exerted onto the distal end element 2 and/or the proximal end element 3, the insulating elements 4 are (slightly) compressed and sealingly about the adjacent metal rings 5.

The connector cavity 1 is intended to receive a connector of at least one electrode or lead that is to be inserted into an interior space of the connector cavity 1.

Figure 2:
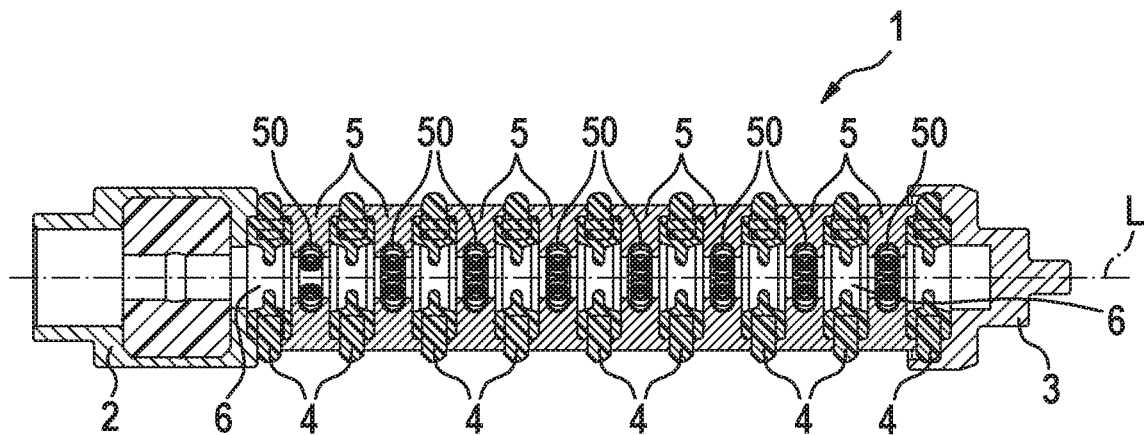
FIG. 2 shows a longitudinal section through the connector cavity of FIG. 1.

This can be seen from FIG. 2 representing a longitudinal section through the connector cavity 1 of FIG. 1. In FIG. 2 and in the following Figures the same numeral references are used for the same or similar elements.

It is apparent, that an interior space 6 of the connector cavity 1 has sufficient space for housing a connector comprising up to eight electrical contacts (each contact contacting a metal spring 50 of the respective metal ring 5). Thus, the connector cavity 1 is suited to receive a connector of a lead having up to eight electrodes.

It is apparent from the depiction of FIG. 2 that the insulation elements 4 electrically insulate two adjacent metal rings 5, whereas each metal ring 5 is in electrical contact with a metal spring 50 centrally arranged surrounding a longitudinal axis L of the connector cavity 1. An electrical contact can be inserted along this longitudinal axis L into the interior space 6 of the connector cavity 1 since each insulating element 4 as well as each metal spring 50 comprises a central opening.

Figure 3A:
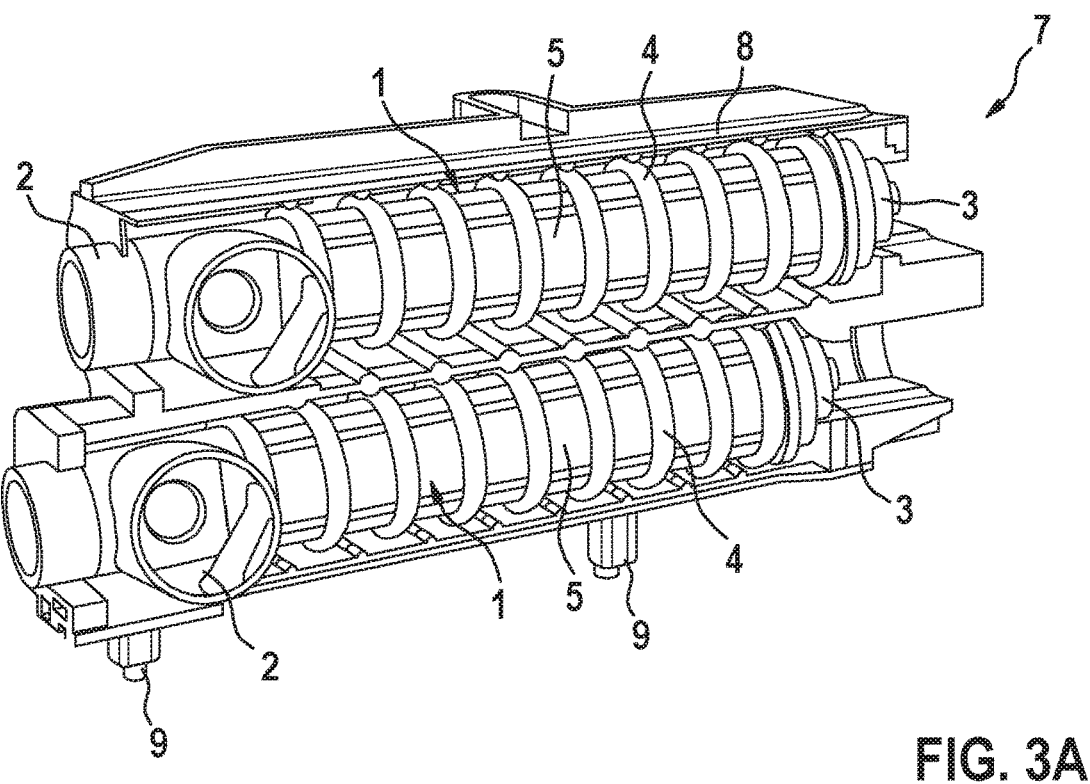
FIG. 3A shows a first view on an embodiment of the connector cavity assembly with two connector cavities.

FIG. 3A shows an embodiment of the connector cavity assembly 7 comprising two constructively identical connector cavities 1 and a connector cavity housing 8 housing both connector cavities 1. For better overview only some of the components of the connector cavities 1 are marked with the respective numeral reference. Reference is made to the explanations given with respect to FIGS. 1 and 2 for explaining the structural details of the connector cavities 1.

The connector cavity housing 8 comprises two connector cavity receiving portions into which the connector cavities 1 are inserted. Thereby, the connector cavity housing 8 directly contacts the respective distal end elements 2 and proximal end element 3 of the connector cavities 1. In doing so, it exerts a pressure onto the distal end elements 2 and the proximal end elements 3 resulting in a pretension of the insulation elements 4 between the conductive metal rings 5. The exerted pressure and thus the resulting pretension is defined by the spatial dimensions of the connector cavity receiving portion, i.e., the distance between a first end portion contacting the distal end element 2 and a second end portion contacting the proximal end element 3 of the respective connector cavity 1. Since this distance is always the same due to a highly standardized manufacturing method (preferably by injection molding) the exerted pressure and the resulting pretension of the connector cavities 1 is also always the same. Even if a high number of connector cavity assemblies 7 is manufactured, the variance between individual connector cavity assemblies 7 is thus very small.

Figure 3B:
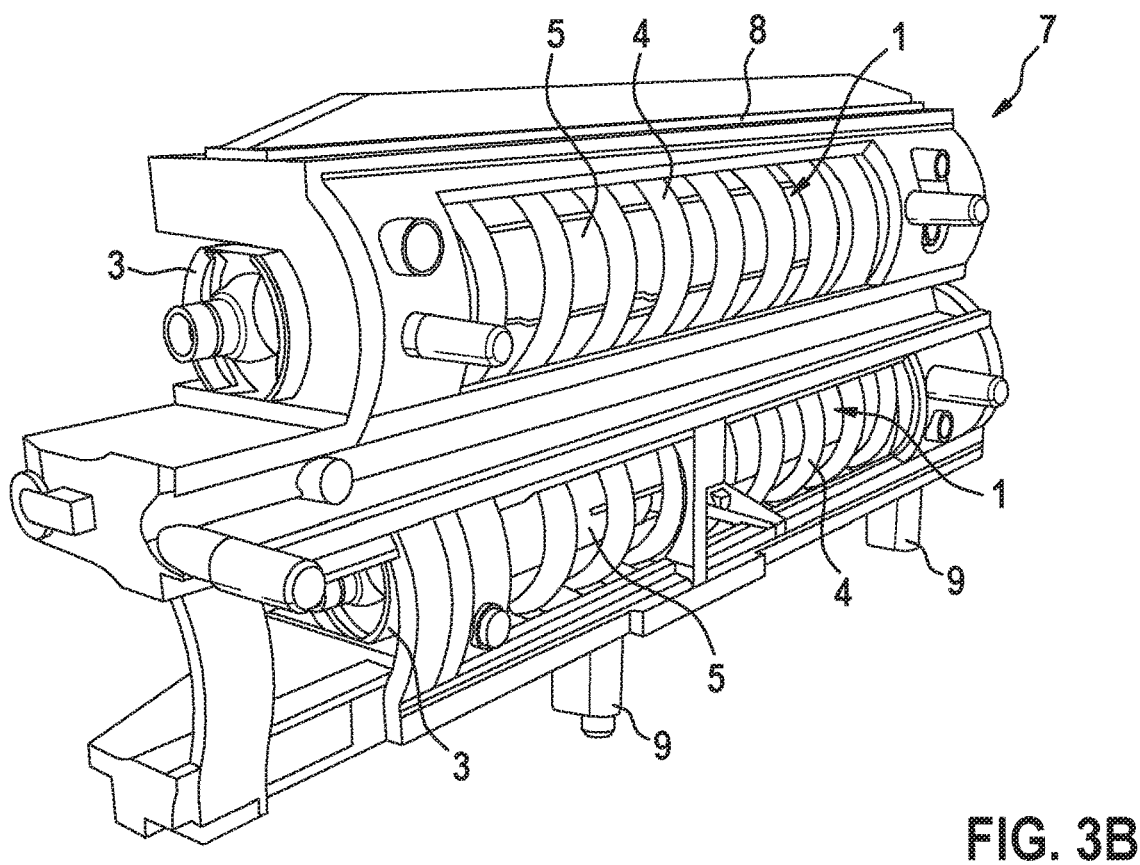
FIG. 3B shows a second view on the connector cavity assembly of FIG. 3A.

FIG. 3B shows the connector cavity assembly 7 of FIG. 3A from the backside. Regarding the individual elements of the connector cavity assembly 7, in particular the connector cavity housing 8 and the inserted connector cavities 1, reference is made to the explanations given with respect to FIG. 3A and the preceding Figures. Like in FIG. 3A and also like in the following Figures, only some of the individual elements of the connector cavity assembly 7 are marked with the respective numeral reference to allow a better overview.

In the depictions of FIG. 3A and FIG. 3B, two spacers 9 can be seen that are provided at a lower side of the connector cavity housing 8. These spacers 9 serve for guaranteeing a defined distance between the connector cavity housing 8 and a body portion of a medical device onto which the connector cavity housing 8 or the connector cavity assembly 7, respectively, is to be applied. FIGS. 4 to 7 particularly illustrates the function of the aforementioned spacers 9. Preferably, the spacers 9 comprise a protruding portion, which is meant to be received by a matching opening or recess on a portion of the above mentioned body portion of the medical device.

Figure 4:
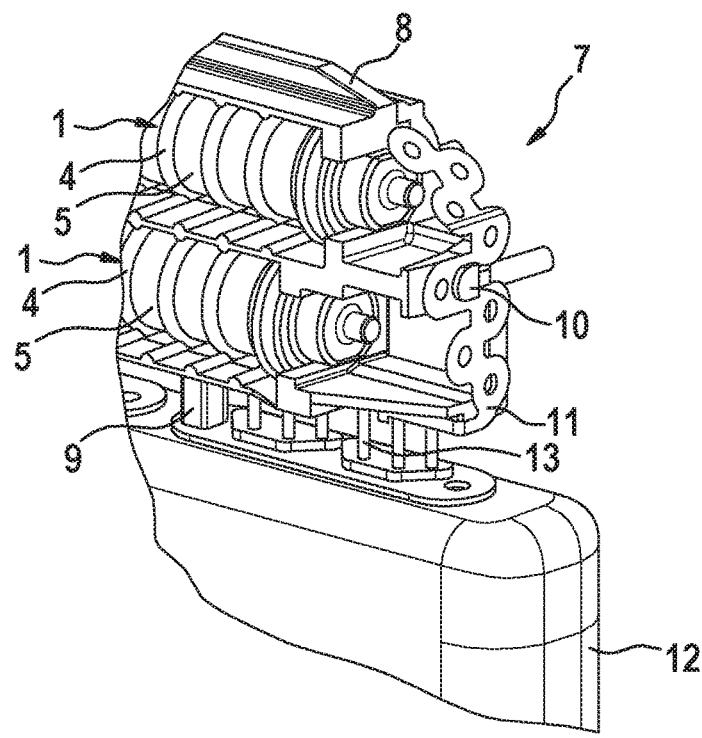
FIG. 4 shows a third embodiment of a connector cavity assembly.

FIG. 4 shows an embodiment of the connector cavity assembly 7, wherein the connector housing 8 comprises a holding element 10 that holds an antenna 11. Thereby, the antenna 11 is clipped onto the holding element 10. It can further be seen from FIG. 4 how the connector cavity assembly 7 is to be placed a body portion 12 of a medical device. Thereby, electrical connectors 13 of the body portion 12, particularly pins 13 extending through the feedthrough 20 of the housing 12 of a medical device, face the mounted connector cavity assembly 7 and enable an electrical connection of individual components of the connector cavity assembly 7 to the body portion 12 of the medical device. Advantageously, the electrical connectors 13 (pins) of the body portion 12 (housing) are fixed to the respective wiring ribbons of the connector cavity assembly 7 by soldering, brazing or welding.

The holding element 10 enables a pre-assembly of the antenna 11 on the connector cavity housing 8 so as to form part of the connector cavity assembly 7. This facilitates a later assembly of the final medical device since the antenna 11 needs no longer be placed into a resin mold upon embedding the antenna 11 and the connector cavities 1 as well as optionally further electrical elements in a resin.

Figure 5:
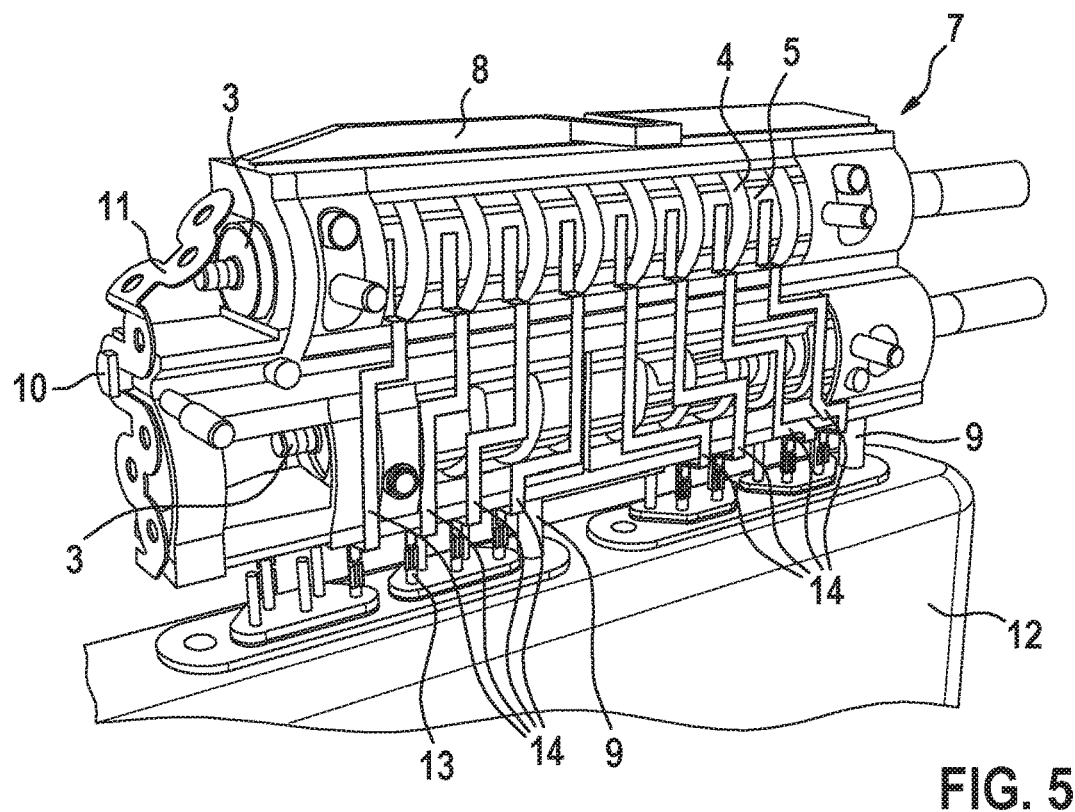
FIG. 5 shows a second embodiment of a connector cavity assembly.

FIG. 5 shows another embodiment of a connector cavity assembly 7 already mounted to the body portion 12 or housing of a medical device. Like the embodiments described with respect to FIG. 4, also the embodiment shown in FIG. 5 comprises an antenna 11 held by a holding element 10 of the connector cavity housing 8 of the connector cavity assembly 7. Furthermore, two connector cavities 1 are inserted into respective connector cavity receiving portions of the connector cavity housing 8. Additionally, a plurality of first wiring ribbons 14 guided in guideways formed on the connector cavity housing 8 is provided. These first wiring ribbons 14 contact the metal rings 5 of the upper connector cavity 1 and thus establish an electric contact between electronics housed in the body portion 12 of the medical device and the metallic springs 50 arranged inside the metal rings 5, particularly via the pins 13 of the feedthrough 20. Since the upper connector cavity 1 is arranged closer to that side oriented towards the front in FIG. 5, the first wiring ribbons 14 do not come into contact with any parts of the lower connector cavity 1, in particular not with any electrically conductive part of the lower connector cavity 1.

Figure 6:
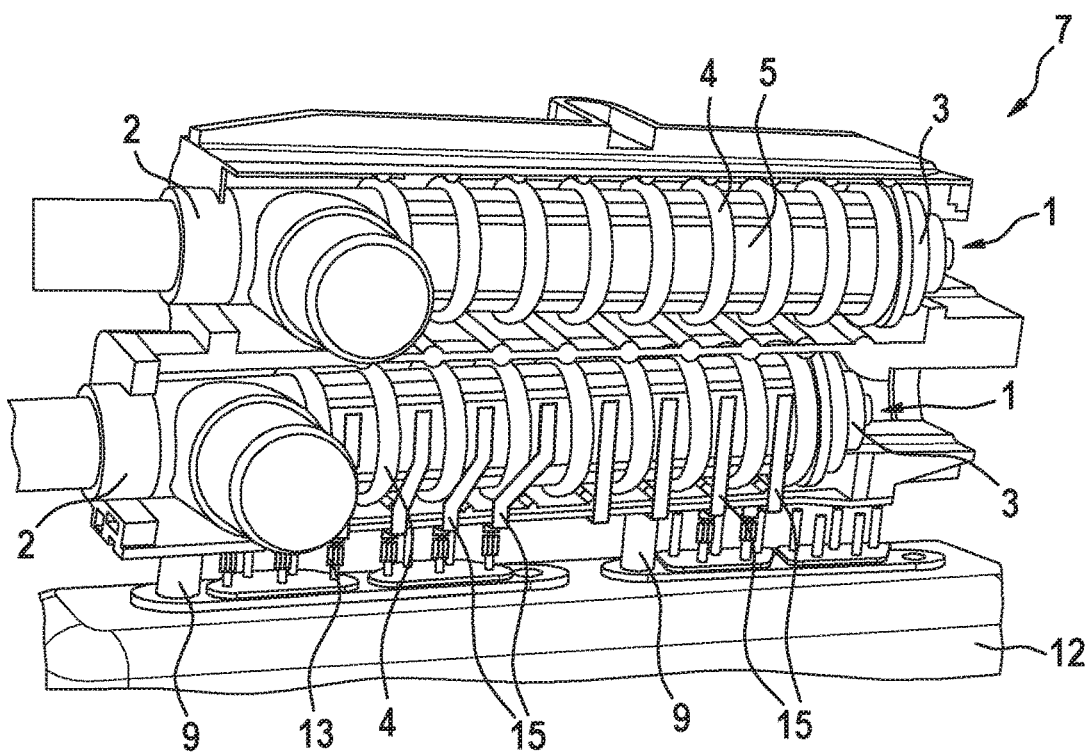
FIG. 6 shows a fourth embodiment of a connector cavity assembly.

FIG. 6 shows another embodiment of the connector cavity assembly 7 with a connector cavity housing 8 and two inserted connector cavities 1. Thereby, the view on this exemplary embodiment of the connector cavity assembly 7 is from the opposite side than the view onto the connector cavity assembly 7 of FIG. 5.

In the embodiment shown in FIG. 6, a plurality of second wiring ribbons 15 is shown guided in guideways formed on the connector cavity housing 8. Since the lower connector cavity 1 is closer to that side of the connector cavity housing 8 that faces to the front in FIG. 6, the second wiring ribbons 15 can easily get in contact with the lower connector cavity 1 and thus establish an electric contact between electronics housed in the body portion 12 or housing of the medical device and the metallic springs 50 arranged inside the metal rings 5.

Figure 7:
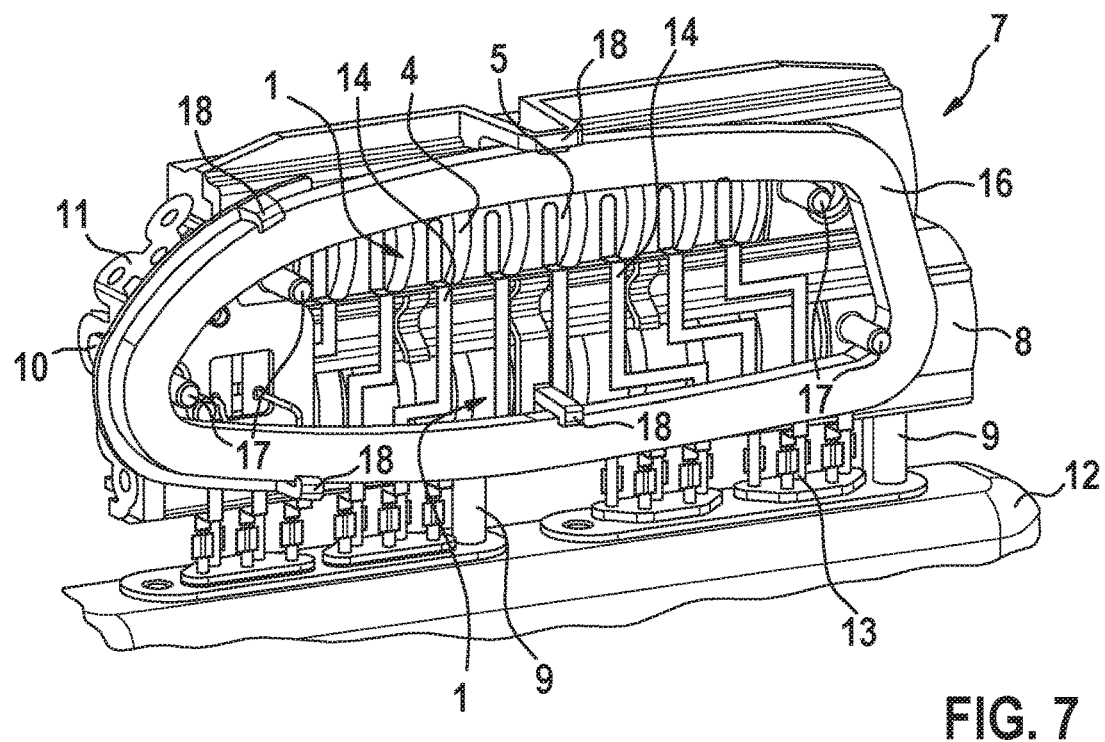
FIG. 7 shows a fifth embodiment of a connector cavity assembly.

FIG. 7 shows another embodiment of the connector cavity assembly 7 with a connector cavity housing 8 and two inserted connector cavities 1. Besides the antenna 11 and the first wiring ribbons 14 already known from the preceding embodiments, this embodiment also comprises an inductive coil 16 for charging a medical device, the connector cavity assembly 7 forms part of. Thereby, the connector cavity housing 8 comprises four guiding pins 17 for guiding the inductive coil 16 as well as four holding clips 18 for holding the conductive coil 16.

By providing these guiding pins 17 it is particularly easy to bring the inductive coil 16 into the correct position on the connector cavity housing 8. Furthermore, the holding clips 18 serve for a tight connection of the inductive coil 16 on the connector cavity housing 8.

It would also be possible to provide holding pins 17 and holding clips 18 without additionally providing a holding element 10 for the antenna 11 and/or without providing guideways for the first wiring ribbons 14 that are all present in the embodiment of FIG. 7. But a combination of these individual elements, i.e., a combination of the precedingly explained embodiments of the connector cavity assembly 7 makes it particularly simple to combine different functionalities into the single connector cavity assembly 7 so as to further facilitate the manufacturing process of a medical device of which the connector cavity 7 forms part of.

It is furthermore easily apparent that the embodiment shown in FIG. 6, i.e., a connector cavity assembly 7 making use of guideways for second wiring ribbons 15 can also be combined with some or all of the other embodiments. Then, both the upper connector cavity 1 and the lower connector cavity 1 can be easily contacted by first and second wiring ribbons 14, 15 guided over respective guideways.

Figure 8:
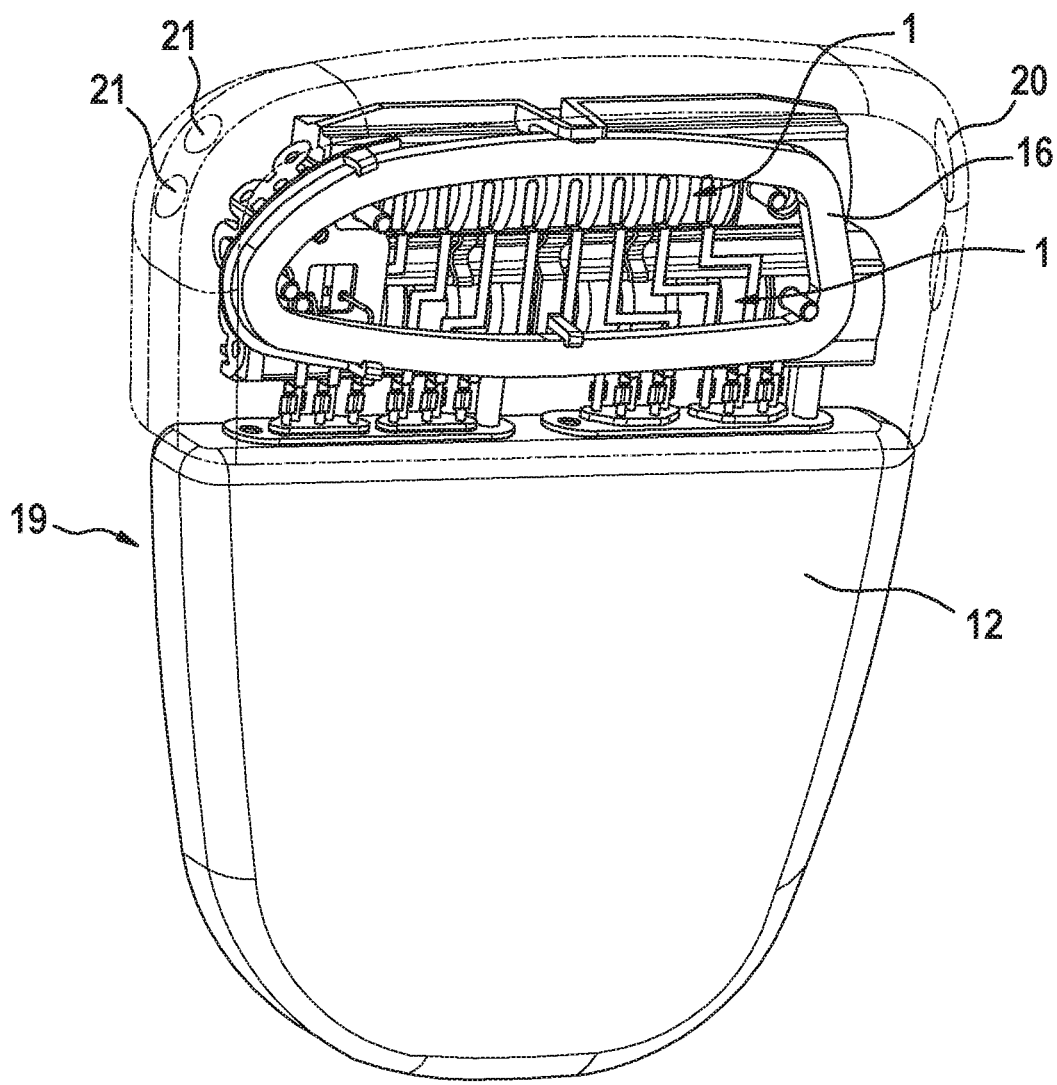
FIG. 8 shows an embodiment of a medical device.

FIG. 8 shows a neurostimulator 19 serving as medical device. It comprises a body portion 12 and a header portion 20. The header portion 20 comprises a resin into which a connector cavity assembly 7, e.g., the embodiment shown in FIG. 7, with an inductive coil 16 is embedded. The resin of the header portion 20 serves for sealing all embedded components with respect to an environment, i.e., with the respect to a body of the patient who carries the neurostimulator 19 as implantable device.

The header portion 20 comprises two connecting ports 21 through each of which a connector of an electrode can be inserted so as to reach the interior of the respective connector cavity 1. In doing so, an electrical contact between the neurostimulator 19 and a connected electrode (not shown in FIG. 8) can be established.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A connector cavity assembly for a medical device, comprising:
    at least one connector cavity comprising a plurality of electrically conductive electrode contacts spaced apart from each other and a plurality of electrically insulating insulation elements, wherein the electrode contacts and the insulation elements are arranged alternatingly along a longitudinal axis, and
    a connector cavity housing,
    wherein the at least one connector cavity is removably arranged within the connector cavity housing, wherein the connector cavity housing is dimensioned so that it exerts a pretension directed along the longitudinal axis on the at least one connector cavity leading to a liquid-tight sealing between the insulation elements and the electrode contacts.

2. The connector cavity assembly according to claim 1, wherein the at least one connector cavity extends in a longitudinal direction from a proximal end to a distal end and comprises a proximal end element positioned at the proximal end and a distal end element positioned at the distal end.

3. The connector cavity assembly according to claim 2, wherein the connector cavity housing is in contact with the connector cavity solely via the distal end element and the proximal end element.

4. The connector cavity assembly according to claim 1, wherein the connector cavity assembly further comprises at least two connector cavities that are offset to each other in a longitudinal direction and/or in a transversal direction of the connector cavity housing.

5. The connector cavity assembly according to claim 1, wherein the connector cavity housing comprises at least one receiving portion for receiving a further component of a medical device.

6. The connector cavity assembly according to claim 5, wherein the at least one receiving portion enables an attachment of a further component of a medical device by a latching connection.

7. The connector cavity assembly according to claim 1, wherein the connector cavity assembly further comprises at least one of an antenna, a coil, and guideways for an external wiring.

8. The connector cavity assembly according to claim 1, wherein the connector cavity housing comprises at least one spacer on its lower side that is intended to face a body portion of a medical device when the connector cavity housing is part of a medical device.

9. A medical device comprising a connector cavity assembly according to claim 1.

10. The medical device according to claim 9, wherein the connector cavity assembly is embedded into a resin, wherein a connecting port is formed in the resin so that an interior of the at least one connector cavity of the connector cavity assembly is accessible from outside the medical device.

11. The medical device according to claim 9, wherein the medical device is an implantable cardiac pacemaker, an implantable cardioverter defibrillator, or an implantable neurostimulator.

12. A method for manufacturing a connector cavity assembly, comprising the following steps:

a) providing a connector cavity housing,
b1) assembling a connector cavity by alternatingly placing electrically conductive electrode contacts and electrically insulating insulation elements into a tensioning device or tool, or
b2) placing a pre-assembled connector cavity comprising alternatingly positioned electrically conductive electrode contacts and electrically insulating insulation elements into a tensioning device or tool,
c) exerting a pretension on the connector cavity with the tensioning device or tool,
d) transferring the pretensioned connector cavity into the connector cavity housing,
e) releasing or removing the tensioning device, and
f) allowing the connector cavity housing to exert a pretension on the connector cavity.

13. The method according to claim 12, wherein the step of assembling the connector cavity or of placing a pre-assembled connector cavity into the pretensioning device is performed without any mandrel being present in an interior space of the connector cavity.

14. The method according to claim 12, wherein the connector cavity housing is a plastic component made by injection molding.

15. A method for manufacturing a medical device, comprising the following steps:

a) providing a connector cavity assembly comprising:
at least one connector cavity comprising a plurality of electrically conductive electrode contacts spaced apart from each other and a plurality of electrically insulating insulation elements, wherein the electrode contacts and the insulation elements are arranged alternatingly along a longitudinal axis, and
a connector cavity housing,
wherein the at least one connector cavity is removably arranged within the connector cavity housing, wherein the connector cavity housing is dimensioned so that it exerts a pretension directed along the longitudinal axis on the at least one connector cavity leading to a liquid-tight sealing between the insulation elements and the electrode contacts,
b) placing the connector cavity assembly on a body of a medical device,
c) establishing an electrical contact between at least one electrically conductive electrode contact of the connector cavity assembly and an electronics housed in the body of the medical device, and
d) casting a hardenable resin around the connector cavity assembly.

* * * * *